(12) United States Patent
Sadowski et al.

(10) Patent No.: US 10,041,915 B2
(45) Date of Patent: Aug. 7, 2018

(54) MASS SPECTROMETRY (MS) IDENTIFICATION ALGORITHM

(71) Applicant: Smiths Detection Inc., Edgewood, MD (US)

(72) Inventors: CHarles S. Sadowski, South Kent, CT (US); Greger Andersson, Oxford, CT (US); Kevin Judge, Southington, CT (US)

(73) Assignee: SMITHS DETECTION INC., Edgewood, MD (US)

( * ) Notice: Subject to any disclaimer, the term of this patent is extended or adjusted under 35 U.S.C. 154(b) by 295 days.

(21) Appl. No.: 14/776,921

(22) PCT Filed: Mar. 14, 2014

(86) PCT No.: PCT/US2014/028331
§ 371 (c)(1),
(2) Date: Sep. 15, 2015

(87) PCT Pub. No.: WO2014/144074
PCT Pub. Date: Sep. 18, 2014

(65) Prior Publication Data
US 2016/0047782 A1 Feb. 18, 2016

Related U.S. Application Data

(60) Provisional application No. 61/788,897, filed on Mar. 15, 2013.

(51) Int. Cl.
*G01N 31/00* (2006.01)
*G01N 30/86* (2006.01)
(Continued)

(52) U.S. Cl.
CPC ..... *G01N 30/8675* (2013.01); *G01N 30/7206* (2013.01); *G01N 30/8686* (2013.01); *G06F 19/703* (2013.01)

(58) Field of Classification Search
CPC ............... G01N 30/72; G01N 30/8658; G01N 30/8679; G01N 30/8693; G01N 30/8655;
(Continued)

(56) References Cited

U.S. PATENT DOCUMENTS 7,873,481 B2 1/2011 Walk et al.
9,512,461 B1 * 12/2016 Beck .................. C12Q 1/04
(Continued)

FOREIGN PATENT DOCUMENTS

DE 10324149 A1 12/2004
WO 2013022771 2/2013

OTHER PUBLICATIONS

PCT/US2014/028331 Search Report and Written Opinion dated Jul. 28, 2014.
(Continued)

*Primary Examiner* — Roy Y Yi
(74) *Attorney, Agent, or Firm* — Advent, LLP; Kevin E. West

(57) ABSTRACT

A system includes a gas chromatograph configured to determine experimental chromatographic data including retention times associated with samples. The system also includes a mass spectrometer configured to determine experimental mass spectral data associated with samples. The mass spectrometer can include a quadrupole field ion trap that uses a non-classical detection technique. The system determines a retention index for an unknown sample based upon retention times for a calibration sample and the unknown sample, and identifies reference mass spectral data using the retention index. The reference mass spectral data can include spectra measured using a classical detection technique. The system can compare the experimental mass spectral data to the reference mass spectral data using one or more comparison metrics, such as a percent fragment match and/or a variance
(Continued)

match. A score can be determined to identify the unknown sample using one or more of the metrics.

19 Claims, 4 Drawing Sheets

(51) Int. Cl.
  *G01N 30/72* (2006.01)
  *G06F 19/00* (2018.01)
(58) Field of Classification Search
  CPC ........... G01N 30/8662; G01N 30/8631; G01N 30/8675; G01N 30/8686; G01N 33/6848; G01N 33/6851; G01N 30/8668; G01N 2030/8813
  See application file for complete search history.

(56) References Cited

U.S. PATENT DOCUMENTS

2006/0255258 A1  11/2006  Wang et al.
2008/0234945 A1*  9/2008  Walk .................. G01N 30/8668
                                          702/19

OTHER PUBLICATIONS

Cornelia Wagner, Michael Sefkow, Joachim Kopka; Construction and application of a mass spectral and retention time index database generated from plant GC/EI-TOF-MS metabolite profiles; Phytochemristry; 62; 2003; pp. 887-900.

Philip A. Smith, Carmela Jackson Lepage, Michael Lukacs, Nicholas Martin, Anton Shufutinsky, Paul B. Savage; Field-portable gas chromatography with transmission quadrupole and cylindrical ion trap mass spectrometric detection: Chromatographic retention index data and ion/moledule interactions for chemical warfare agent identifidcation; International Journal of Mass Spectrometry; 295; 2010; pp. 113-118.

Maria Ibanez, Juan V. Sancho, Oscar J. Pozo, Wilfried Niessen, and Felix Hernandez; Use of Quadrupole time-of-flight mass spectrometry in the education of unknown compounds present in environmental water; Rapid Communications in Mass Spectrometry; 2005; 19; pp. 169-178.

Extended European Search Report dated Oct. 14, 2016 for EP Appln. No. 14764633.5.

Diken, Eric G. et al., "Advances in field-portable ion trap GC/MS instrumentation", Optical Sensing II, vol. 8358, Apr. 23, 2012, p. 83581H.

Efficient Screening for Pesticides and Endocrine Disrupters Using the 6890/5973 GC/MSD System, Internet Citation, May 1999, XP002293692.

* cited by examiner

MASS SPECTROMETRY (MS) IDENTIFICATION ALGORITHM

BACKGROUND

Gas chromatography (GC) is a chromatographic technique used to separate and analyze compounds that can be vaporized without decomposition. Mass spectrometry (MS) is an analytical technique used to measure mass-to-charge ratios of charged particles in the form of molecules, molecule fragments, and/or atoms, which can be generated from ionized sample materials. MS can be used to determine particle masses, elemental composition, and/or chemical structures of sample material. Gas chromatography-mass spectroscopy (GC-MS) combines a gas chromatograph with a mass spectrometer. Together, gas chromatography and mass spectroscopy often provide a finer degree of sample identification than either technique can provide separately. For instance, mass spectrometry generally requires a pure sample, while gas chromatography may not be capable of differentiating between different molecules with the same retention times. However, because it is unlikely that two different molecules will have the same behavior with respect to both a gas chromatograph and a mass spectrometer, there can be an increased certainty that a particular analyte is present in a sample of interest when an identifying mass spectrum appears at a characteristic retention time in a GC-MS analysis.

SUMMARY

Systems and techniques for sample detection using, for example, gas chromatography-mass spectroscopy (GC-MS) systems are described. For instance, a GC-MS system includes a gas chromatograph configured to determine experimental chromatographic data for a calibration sample and an unknown sample, where the experimental chromatographic data includes a first retention time associated with the calibration sample and a second retention time associated with the unknown sample. The GC-MS system also includes a mass spectrometer configured to determine experimental mass spectral data for the unknown sample, where the experimental mass spectral data includes a mass spectrum associated with the unknown sample. In implementations, the mass spectrometer is configured as a quadrupole field ion trap, such as a toroidal ion trap, and produces in many instances a non-classical mass spectrum.

A processor is communicatively coupled with the gas chromatograph and the mass spectrometer for receiving the experimental chromatographic data and the experimental mass spectral data. The processor is configured to determine a retention index for the unknown sample based upon the first retention time associated with the calibration sample and the second retention time associated with the unknown sample. The processor is also configured to identify a subset of database entries in an electronic database of reference mass spectral data using the retention index. In implementations, the electronic database includes spectra measured primarily using a classical detection technique, such as a quadrupole mass spectrometer (QMS). The system compares the experimental mass spectral data to the subset of database entries to identify the unknown sample.

In implementations, the system compares the experimental mass spectral data to the subset of database entries to identify the unknown sample using one or more comparison metrics, such as a percent fragment match between the experimental mass spectral data and the subset of database entries and/or a variance match between the experimental mass spectral data and the subset of database entries between the experimental mass spectral data and the subset of database entries. In some instances, a score can be determined using one metric, a combination of two or more metrics, and/or a weighted combination of two or more metrics. The score can be used to determine a match between the unknown sample and an electronic database entry, and the sample can be identified accordingly.

Whereas these algorithms fundamentally use a like versus like method for identification. A difference in the mass spectrum generated by a mass analyzer that produces a non-classical spectrum, such as an Ion Trap mass spectrometer, is that it hinders accurate identification. The pre-search and identification methods described here present an alternate approach that allows accurate identification when searching ion trap mass spectra against a database of more classical mass spectra generated by a quadrupole mass analyzer, for example.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Figure 1:
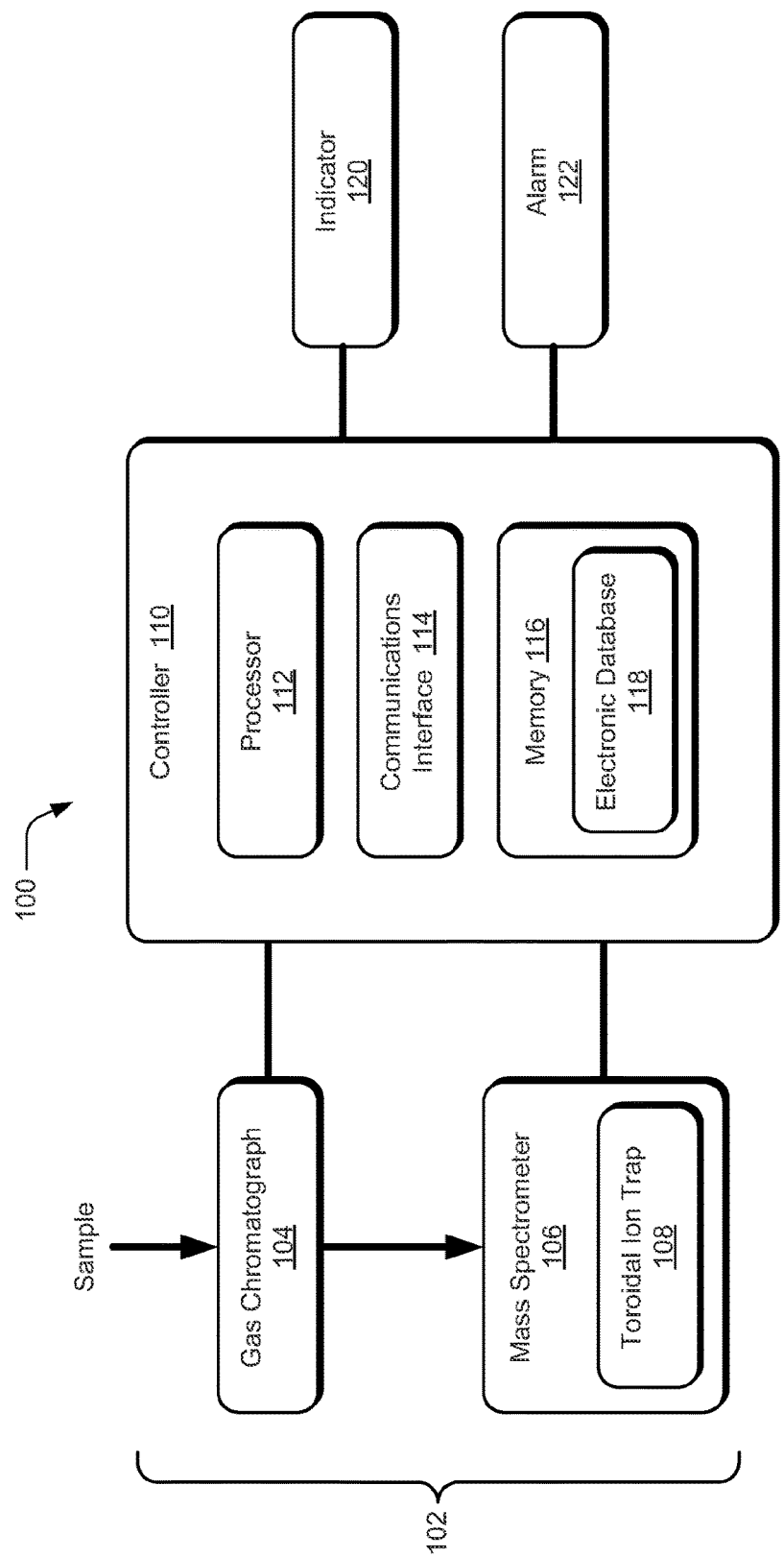
FIG. 1 is a block diagram illustrating a GC-MS system including a gas chromatograph and a mass spectrometer for collecting mass spectral data from a sample injection using a non-classical detection technique, where the GC-MS system employs an electronic database including spectra measured using a classical detection technique in accordance with an example implementation of the present disclosure.

Gas chromatography-mass spectroscopy (GC-MS) combines a gas chromatograph with a mass spectrometer. Generally, a gas chromatograph uses a capillary column having particular dimensions (e.g., length, diameter, and film thickness) and phase properties. Differences in chemical properties between different molecules in a sample cause the molecules to separate as the sample travels the length of the column. For instance, an adsorbent can be used to adsorb analytes in a chromatography column. The molecules of the analytes are retained by the column and then elute from the column at different times (referred to as retention times). A mass spectrometer downstream from a gas chromatograph can then detect the ionized molecules separately, e.g., by breaking a molecule into ionized fragments and detecting the fragments using mass-to-charge ratios. Thus, the mass spectrometer can be used to ionize the analytes, separate the resulting ions according to their mass-to-charge ratios, detect the ions, generate signals based upon the detected ions, and process the resulting detected ion signals into mass spectra, from which the analytes can be identified.

A quadrupole mass spectrometer (QMS) is a mass analyzer that uses four (4) parallel rods to filter sample ions based upon their mass-to-charge ratios. Oscillating electric fields are applied to the parallel rods, and ions travelling between the rods are separated based upon the stability of their trajectories in the electric fields. For example, as ions travel longitudinally through the quadrupole, ions having a particular mass-to-charge ratio will reach a detector at the end of the quadrupole, while other ions having different mass-to-charge ratios will have unstable trajectories and will collide with the rods. In this manner, particular ions can be detected by controlling the operating characteristics of a quadrupole (e.g., by controlling voltages applied to pairs of opposing rods of the quadrupole).

A quadrupole ion trap uses the same physical principles as a QMS, but traps and sequentially ejects ions rather than causing them to collide with the instrumentation. For example, ions can be trapped by a three-dimensional (3-D) quadrupole field in a space defined by a ring electrode positioned between two end-cap electrodes. One technique for mass-to-charge ratio separation and/or isolation of trapped ions uses mass instability, where the orbits of trapped ions with greater masses remain stable, while the orbits of other trapped ions with less mass become unstable and the ions are ejected (e.g., onto a detector). Another technique for separating and/or isolating trapped ions uses resonance excitation, where various trapped ions are brought into a resonance condition in order of their mass-to-charge ratios. A linear quadrupole ion trap traps ions in a two-dimensional (2-D) quadrupole field as opposed to a 3-D quadrupole field. A toroidal ion trap can be described as a linear quadrupole trap having a ring-like structure connected at both ends, and can store large volumes of ions throughout its toroid trap structure. This configuration can be used to provide miniaturized ion trap mass analyzers. Further, because the ions are all stored in a common field in a toroidal ion trap, detection can be simplified as ions are ejected from the field together, e.g., as opposed to a configuration that requires an array of detectors.

However, reference mass spectral data used for analyte identification is typically compiled using classical detection techniques, such as QMS detection. When a non-classical technique is employed, such as detection performed using a toroidal ion trap, there can be discrepancies between experimental and reference mass spectral data. This applies to all types of ion traps. For example, a National Institute of Standards and Technology (NIST) database can be used as a reference library for sample identification. Such a database often includes spectra measured primarily on QMS systems. Use of, for instance, a toroidal trap configuration can potentially lead to mass spectral differences when the data is analyzed using a QMS database. These differences can include relative intensity variations, the creation of additional fragments based upon ion chemistry, and so forth.

Techniques are described for identifying unknown samples using a system including a gas chromatograph configured to determine experimental chromatographic data including retention times associated with samples, and a mass spectrometer configured to determine experimental mass spectral data associated with the samples. The mass spectrometer can include, a quadrupole field ion trap that uses a non-classical detection technique. The system determines a retention index, for an unknown sample based upon retention time for a calibration sample and the unknown sample, and identities reference mass spectral data using the retention index as a fundamental part of the pre-search algorithm. The reference mass spectral data can include spectra measured using a classical detection technique. The system can compare the experimental mass spectral data to the reference mass spectral data using one or more comparison metrics, such as a percent fragment match and/or a variance match. A score can be determined to identify the unknown sample using one or more of the metrics.

Referring to FIG. 1, a gas chromatography-mass spectroscopy (GC-MS) system 100 includes GC-MS instrumentation 102, such as a gas chromatograph 104 and a mass spectrometer 106. The gas chromatograph 104 is configured to determine experimental chromatographic data for a sample injection (e.g., for a calibration sample, an unknown sample, and so forth), where the experimental chromatographic data comprises a retention time associated with each compound in the sample. The mass spectrometer 106 is configured to determine experimental mass spectral data for the sample injection, where the experimental mass spectral data comprises a mass spectrum associated with each compound in the sample. The mass spectrometer 106 employs a non-classical detection technique. For example, the mass spectrometer 106 may use a toroidal ion trap 108 for sample detection. In implementations, a controller 110 is operatively coupled with the gas chromatograph 104 and the mass spectrometer 106 for receiving the experimental chromatographic data and the experimental mass spectral data from the GC-MS instrumentation 102. The GC-MS system 100 is configured to identify samples introduced to the GC-MS instrumentation 102 (e.g., using the controller 110).

In implementations, a GC-MS system 100, including some or all of its components, can operate under computer control. For example, a processor can be included with or in a GC-MS system 100 to control the components and functions of GC-MS systems 100 described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the GC-MS systems 100. In the case of a software implementation, the module, functionality, or logic represents program code that performs specified tasks when executed on a processor (e.g., CPU or CPUs). The program code may be stored in one or more computer-readable memory devices (e.g., internal memory and/or one or more tangible media), and so on. The structures, functions, approaches, and techniques described herein can be implemented on a variety of commercial computing platforms having a variety of processors.

As illustrated in FIG. 1, the GC-MS instrumentation 102 may be coupled with the controller 110 for controlling the gas chromatograph 104 and the mass spectrometer 106. The controller 110 may include a processor 112, a communications interface 114, and a memory 116. The processor 112 provides processing functionality for the controller 110 and may include any number of processors, micro-controllers, or other processing systems, and resident or external memory for storing data and other information accessed or generated by the controller 110. The processor 112 may execute one or more software programs that implement techniques described herein. The processor 112 is not limited by the materials from which it is formed or the processing mechanisms employed therein and, as such, may be implemented via semiconductor(s) and/or transistors (e.g., using electronic integrated circuit (IC) components), and so forth.

The communications interface 114 is operatively configured to communicate with components of the GC-MS system 100. For example, the communications interface 114 can be configured to transmit data for storage in the GC-MS system 100, retrieve data from storage in the GC-MS system 100, and so forth. The communications interface 114 is also communicatively coupled with the processor 112 to facilitate data transfer between components of the GC-MS system 100 and the processor 112 (e.g., for communicating inputs from the GC-MS instrumentation 102 to the processor 112). The communications interface 114 and/or the processor 112 can also be configured to communicate with a variety of different networks, including, but not necessarily limited to: the Internet, a cellular telephone network, a local area network (LAN), a wide area network (WAN), a wireless network, a public telephone network, an intranet, and so on. In FIG. 1, the communications interface 114 is illustrated as a component of the GC-MS system 100. However, one or more components of the communications interface 114 can be implemented as external components communicatively coupled to the GC-MS system 100 via a wired and/or wireless connection. The GC-MS system 100 can also comprise and/or connect to one or more input/output (I/O) devices (e.g., via the communications interface 114), including, but not necessarily limited to: a display, a mouse, a touchpad, a keyboard, and so on.

The memory 116 is an example of tangible computer-readable storage medium that provides storage functionality to store various data associated with operation of the controller 110, such as software programs and/or code segments, or other data to instruct the processor 112 and possibly other components of the controller 110 to perform the steps described herein. Thus, the memory 116 can store data, such as a program of instructions for operating the GC-MS system 100 (including its components), spectral data, and so on. The memory 116 can include an electronic database 118 comprising reference mass spectral data for identifying samples provided to the GC-MS system 100. In a particular instance, the electronic database 118 can be a NIST database including spectra measured on a QMS system. Although a single memory 116 is shown, a wide variety of types and combinations of memory (e.g., tangible, non-transitory memory) may be employed. The memory 116 may be integral with the processor 112, may comprise standalone memory, or may be a combination of both.

The memory 116 may include, but is not necessarily limited to: removable and non-removable memory components, such as random access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the GC-MS instrumentation 102 and/or memory 116 may include removable integrated circuit card (ICC) memory, such as memory provided by a subscriber identity module (SIM) card, a universal subscriber identity module (USIM) card, a universal integrated circuit card (UICC), and so on.

In implementations, a variety of analytical devices can make use of the structures, techniques, approaches, and so on described herein. Thus, although GC-MS systems 100 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Example Procedures

The following discussion describes procedures that may be implemented utilizing the previously described GC-MS system 100 components, techniques, approaches, and modules. Aspects of each of the procedures may be implemented in hardware, software, or a combination thereof. The procedures are shown as a set of blocks that specify operations performed by one or more devices (e.g., GC-MS instrumentation, a computer system controlling GC-MS instrumentation or GC-MS components) and are not necessarily limited to the order shown for performing the operations by the respective blocks. In portions of the following discussion, reference will be made to the GC-MS systems 100 of FIG. 1.

Figure 2:
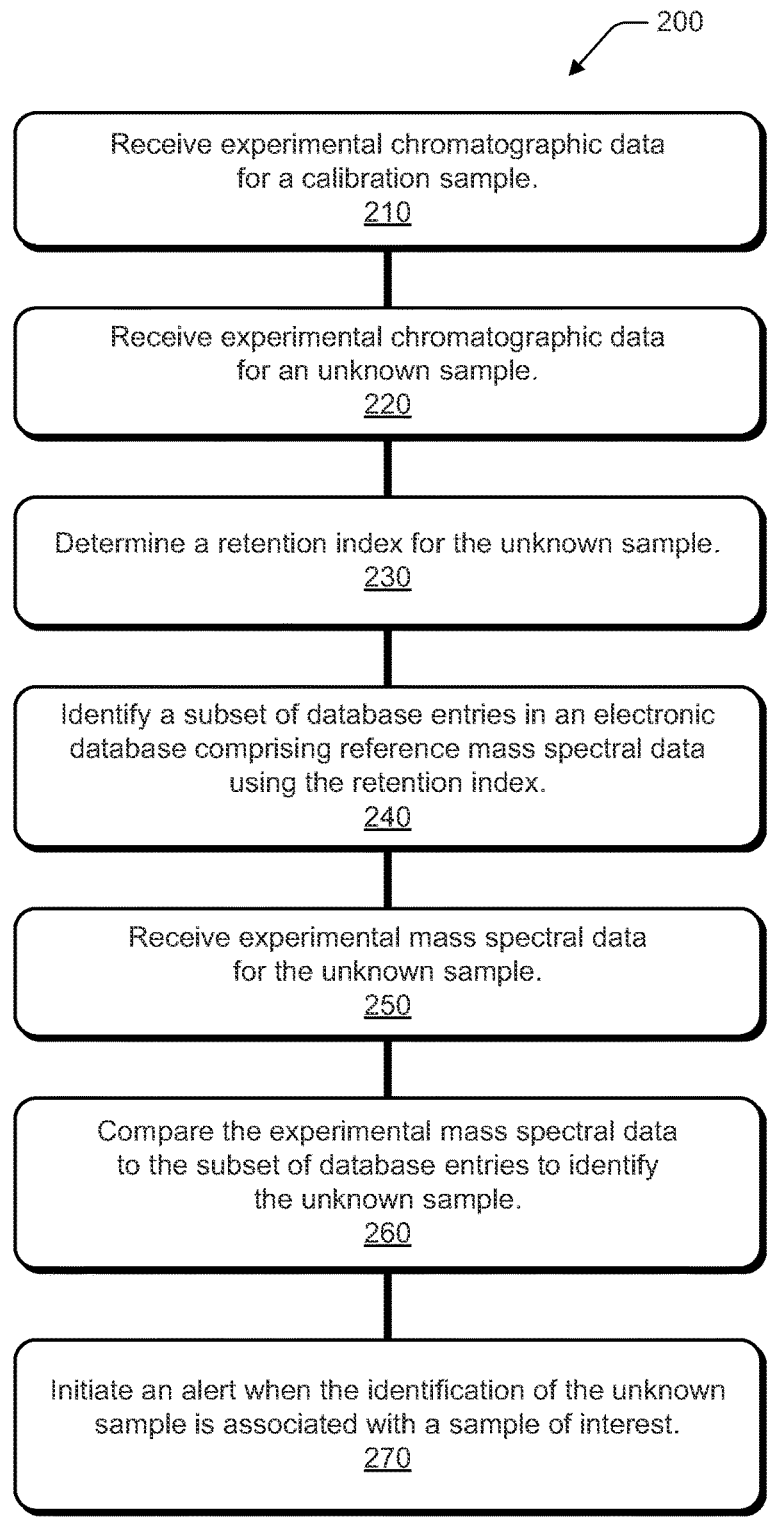
FIG. 2 is a flow diagram illustrating a method for identifying an unknown sample using a gas chromatograph, a non-classical mass spectrometer detection technique, and an electronic database including spectra measured using a classical detection technique in accordance with an example implementation of the present disclosure.

FIG. 2 depicts a procedure 200 in an example implementation in which experimental chromatographic data is received for a calibration sample (Block 210). For example, with reference to FIG. 1, the gas chromatograph 104 can be used to determine experimental chromatographic data including a retention time for a calibration sample injection, and the experimental chromatographic data can be supplied to the controller 110. Then, experimental chromatographic data is received for an unknown sample (Block 220). For instance, with continuing reference to FIG. 1, the gas chromatograph 104 can be used to determine experimental chromatographic data including a retention time for an unknown sample injection, and the experimental chromatographic data can be supplied to the controller 110. Next, a retention index is determined for the unknown sample (Block 230). For example, with continuing reference to FIG. 1, the controller 110 can be configured to determine a retention index for the unknown sample based upon the retention time for the calibration sample and the retention time for the unknown sample. In implementations, the retention index can be one or more retention times and/or a range of retention times.

Then, a subset of database entries in an electronic database comprising reference mass spectral data is identified using the retention index (Block 240). For instance, with continuing reference to FIG. 1, the controller 110 can identify one or more database entries in the electronic database 118 stored in the memory 116 of the controller 110 based upon the retention index for the unknown sample. In a particular instance, the electronic database 118 is a NIST database in which each library entry comprises a retention index and an allowed deviation. The retention indices in the NIST database can be compared to the retention index for the unknown sample (e.g., using a retention index window comprising multiple retention times and/or a range of retention times) and used to filter the database, reducing the number of potential candidates from the electronic database 118. In some instances, the retention index for the unknown sample can be retained (e.g., in the memory 116) and used to correlate a probability to how well the retention indices selected from the electronic database 118 correlate to the retention index determined for the unknown sample, e.g., after sample identification.

Next, experimental mass spectral data is received for the unknown sample (Block 250). For example, with continuing reference to FIG. 1, the mass spectrometer 106 can be used to determine experimental mass spectral data including a mass spectrum for the unknown sample, and the experimental mass spectral data can be supplied to the controller 110. Then, the experimental mass spectral data is compared to the subset of database entries to identify the unknown sample (Block 260). For instance, with continuing reference to FIG. 1, one or more database entries in the electronic database 118 stored in the memory 116 can be compared to the experimental mass spectral data to identify the unknown sample (e.g., as described below with reference to Blocks 320 through 360 of FIG. 3). In embodiments of the disclosure, the controller 110 is configured to initiate an alert when the identification of the unknown sample is associated with a sample of interest (Block 270). For example, with continuing reference to FIG. 1, the controller 110 is configured to detect the presence of explosive and/or chemical agents and provide a warning or indication of such agents. An alert can be initiated at an indicator 120, an alarm 122, the indicator 120 and the alarm 122, and so forth. In some embodiments, the indicator 120 comprises an electronic display, one or more indicator lights, and so on. Further, the alarm 122 can furnish an audible alarm, a visual alarm (e.g., an indicator light), a tactile alarm, a signal transmitted to a remote monitoring authority, and so forth. However, these alerts are provided by way of example only and are not meant to limit the present disclosure. In other embodiments, different or additional alerts are initiated by the controller 110 (e.g., using the indicator 120, the alarm 122, or another alert mechanism). For example, an alert is initiated in the form of an electronic message, such as an email message, a text message, and so on.

Figure 3:
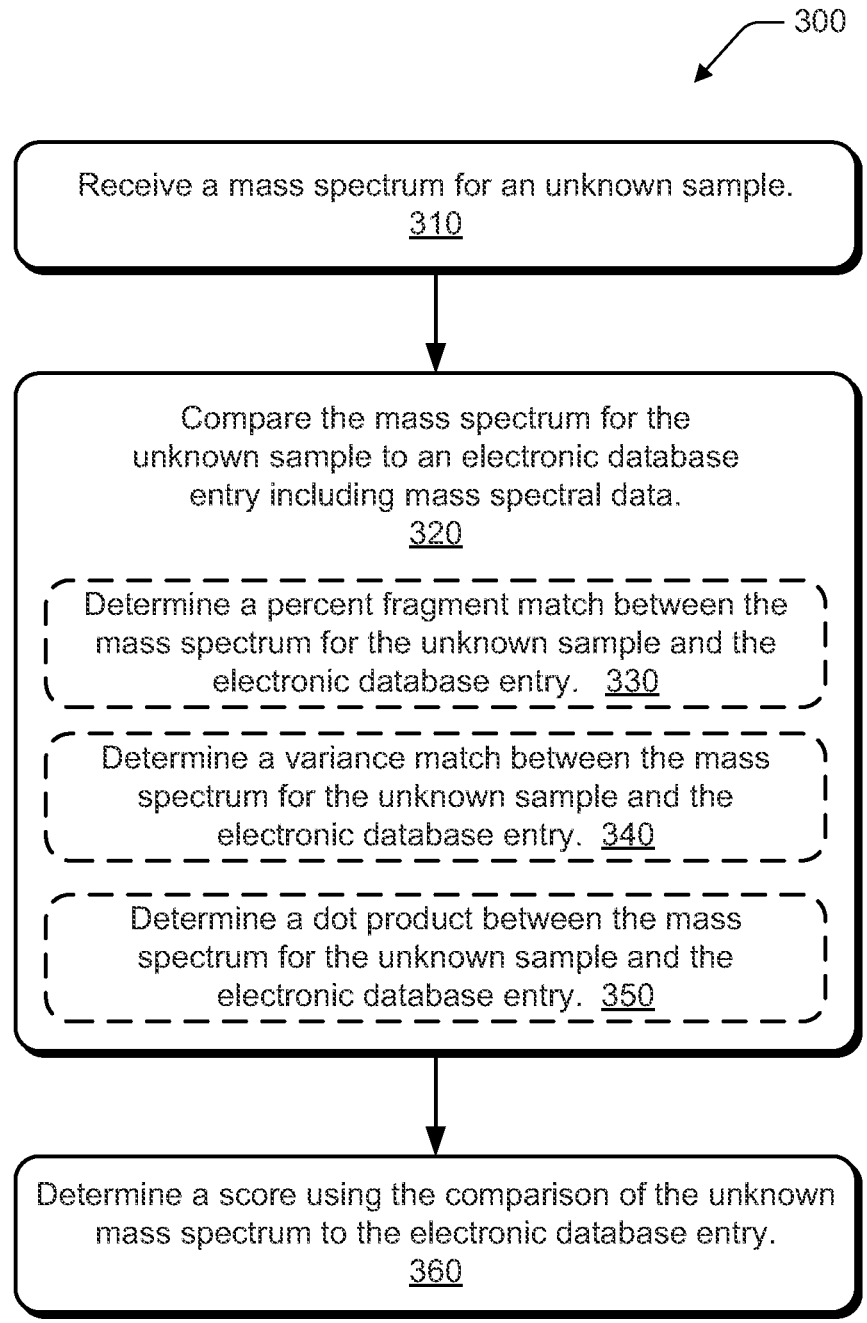
FIG. 3 is a flow diagram illustrating a method for comparing experimental mass spectral data to one or more electronic database entries to identify an unknown sample in accordance with an example implementation of the present disclosure.

Referring now to FIG. 3, an example procedure 300 is described in which a mass spectrum is received for an unknown sample (Block 310). The mass spectrum can be received from a mass spectrometer, such as the mass spectrometer 106 of FIG. 1 (e.g., as described above with reference to Block 250 of FIG. 2). The mass spectrum may be represented using a peak table (e.g., as illustrated by the "Unknown Spectrum" graph of FIG. 4). In implementations, the mass spectrum includes a list of mass fragments and their relative abundances.

Then, the mass spectrum for the unknown sample is compared to an electronic database entry including mass spectral data (Block 320). For example, with continuing reference to FIG. 1, an initial comparison can be performed for the unknown sample using one or more of the database entries in the electronic database 118 stored in the memory 116 (e.g., as identified above with reference to Block 240 of FIG. 2 and illustrated by the "Library Spectrum" graph of FIG. 4). In a particular instance, an initial comparison is performed by counting the number of mass fragments common to both the unknown sample and the electronic database entry. A temporary score can be calculated using the mean percentage of mass fragments matched as follows:

$$\text{fragMatch} = [(n_{common}/n_{unk}) + (n_{common}/n_{lib})]/2$$

where $n_{common}$ represents the number of common mass fragments, $n_{unk}$ represents the total number of mass fragments in the unknown mass spectrum, and $n_{lib}$ represents the total number of mass fragments in the electronic database spectrum.

In some instances, mass fragments below a mass of forty-three (43) and above a mass of five hundred (500) are excluded from the comparison (e.g., when these mass fragments are not measured by the mass spectrometer). Further, mass fragments having an intensity of less than five percent (5%) of the base peak can be ignored (e.g., to account for a signal-to-noise ratio). As described herein, elimination of mass fragments will not penalize the hit quality when the mass fragments are absent from the electronic database spectrum. In this particular implementation, an electronic database entry must have at least one mass fragment in common with the unknown spectrum, otherwise the hit score fragMatch will be zero (0).

However, comparing mass fragments between a mass of forty-three (43) and above a mass of five hundred (500) is provided by way of example only and is not meant to be restrictive of the present disclosure. Thus, in other instances, more or fewer mass fragments can be compared. For example, in a particular instance, one peak, two peaks, or more than two peaks (e.g., three peaks) can be used to filter or pre-filter the electronic database entries used for the comparison. In some instances, the peaks chosen for the comparison can be based upon the heaviest mass fragments. In other instances, the peaks chosen for the comparison can be the most intense peaks. Further, one or more analytic techniques, such as a rule of transient data fusion, can be used to determine which peaks may be most unique and/or best suited for the comparison.

Figure 4:
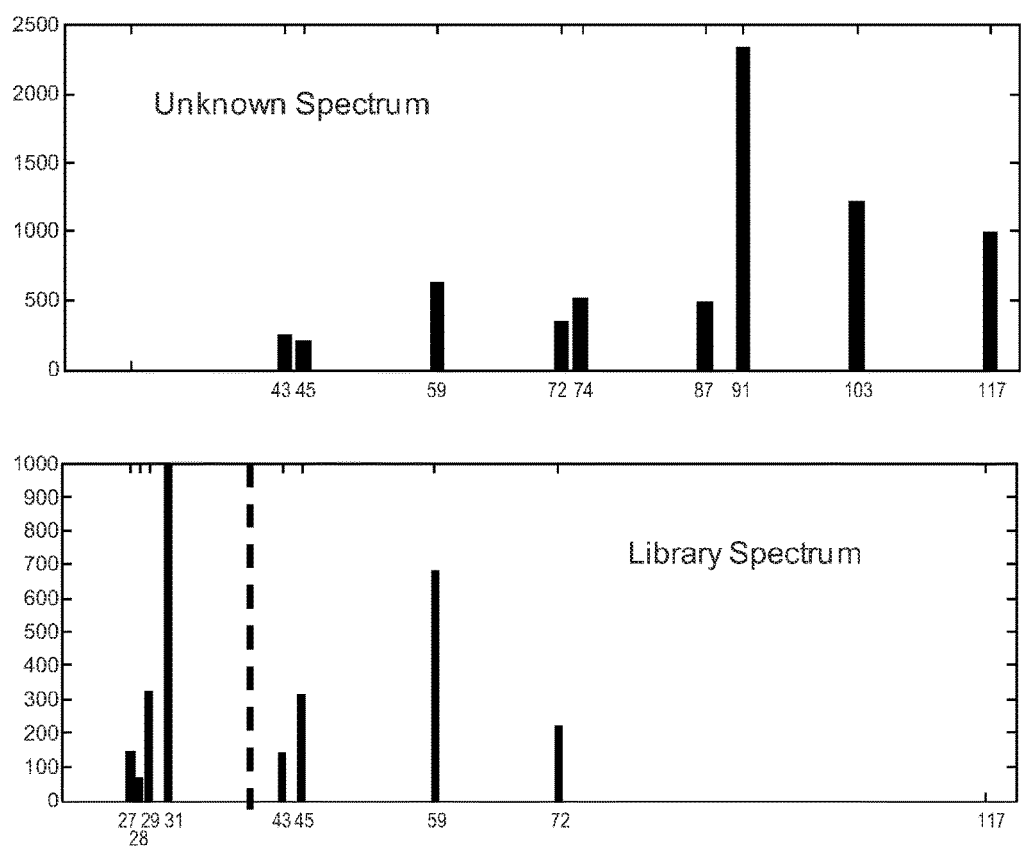
FIG. 4 is a series of graphs illustrating a comparison between an unknown mass spectrum and a library spectrum for 2-ethoxy-ethanol.

In an implementation where an ion trap is used, such as a toroidal ion trap, and so forth, ion chemistry is often observed in mass spectra from the trap system. The most common types of ion chemistry are the formation of an M+1 mass fragment, a 2M, 2M+1 mass fragment in dimers, and the combination of other mass fragments with a neutral molecule. An M+1 mass fragment is equal to the molecular weight of the chemical plus a value of one (1). As illustrated in FIG. 4, the occurrence of ion chemistry can explain some of the differences seen in the mass spectra for 2-ethoxy-ethanol. For instance, knowing 2-ethoxy-ethanol has a molecular weight of ninety (90), two of the higher mass fragments present in the unknown can be explained. The mass fragment at mass ninety-one (91) represents the M+1 mass fragment. The mass fragment at mass one hundred and seventeen (117) results from a combination of the neutral mass ninety (90) with the lower ion at mass twenty-seven (27).

A percent fragment match can be determined between the mass spectrum for the unknown sample and the electronic database entry (Block 330). For example, after the initial search for common mass fragments, the mass spectrum for the unknown sample is compared to the electronic database entry by searching for ion chemistry. In implementations, the term $n_{common}$ in the above equation can be replaced by the terms $n_{foundUnk}$ and $n_{foundLib}$ as follows:

$$\text{fragMatch} = [(n_{foundUnk}/n_{unk}) + (n_{foundLib}/n_{lib})]/2$$

In this manner, using the known molecular weight for a specific electronic database entry, a search for the presence of ion chemistry mass fragments such as M+1 and 2M+1 in the unknown spectrum is performed. If detected, the number of found unknown mass fragments, $n_{foundUnk}$, will increase by a value of one (1) (or two (2) when both are present). If the electronic database spectrum contains a mass fragment at M, the entry's molecular weight, it will also be considered a match, but only if M+1 or 2M+1 is found in the unknown mass spectrum.

The molecular weight of the electronic database entry is then added to all of the electronic database mass fragments (including fragments with mass less than the forty-three (43) cutoff in some implementations). These adjusted electronic database mass fragments are then used for comparison in a final pass through the unknown mass fragments. If there are any new matches, $n_{foundUnk}$ will be increased. It should be noted that in some instances (e.g., when it is not necessarily desirable to count ion chemistry hits as true matches), the increment could be less than a value of one (1). The term $n_{foundLib}$ may also be increased, e.g., if the original mass fragment met the initial restrictions. Otherwise, it may not be accounted for in the denominator, $n_{lib}$. With reference to FIG. 4, the percent mass fragment factor for 2-ethoxy-ethanol can be calculated as follows:

$$fragMatch=[(6/9)+(4,4)]/2=0.833$$

where $n_{foundUnk}$ is equal to six (6), $n_{Unk}$ is equal to nine (9), $n_{foundLib}$ is equal to four (4), and $n_{Lib}$ is equal to four (4).

In addition to the mean percent mass fragment match after allowing for ion chemistry, two other criteria can be combined to generate a final hit score. Because heavier mass fragments are more distinctive, spectra can be scaled to emphasize the larger mass fragments in the calculations of the next two factors. The intensities can be scaled based upon the following equation:

$$w(i)=m(i)*x(i)$$

where $x(i)$ represents the original intensity of the ith mass fragment, $m(i)$ is the mass-to-charge ratio of the ith mass fragment, and $w(i)$ is the scaled intensity for the ith mass fragment. The mass spectra of the remaining identified electronic database candidates can also be scaled.

A variance match can be determined between the mass spectrum for the unknown sample and the electronic database entry (Block 340). For instance, a second metric can be determined in a manner similar to the percent mass fragment match described above, but counting variance instead of mass fragments. Different from the percent mass fragment match, the variance match can be a product of the two spectra's contributions, given as follows:

$$varMatch=(var_{foundUnk}/(var_{totUnk}))*(var_{foundLib}/(var_{totLib}))$$

where the terms $var_{totUnk}$ and $var_{totLib}$ represent the total variance of the mass-scaled unknown spectrum and electronic database spectrum, respectively, calculated as follows:

$$var_{tot}=\Sigma w(i)^2$$

where $w(i)$ squared represents the variance contribution of a single mass fragment. The found variance terms, $var_{foundUnk}$ and $var_{foundLib}$, are determined as follows:

$$var_{found}=\Sigma a(i)*w(i)^2$$

where $a(i)$ is equal to a value of one (1) to indicate a matched mass fragment and equal to a value of zero (0) if the ith mass fragment is not found. It should be noted that in some instances, it may not necessarily be desirable to weight ion chemistry matches as much as true matches, and, as such, an $a(i)$ value between zero (0) and one (1) can be used.

A dot product can be determined between the mass spectrum for the unknown sample and the electronic database entry (Block 350). For instance, a third metric can be a weighted dot product between the scaled unknown mass spectrum and the electronic database spectra. The dot product can be calculated as follows:

$$wDP=\Sigma w_{lib}(i)*w_{unk}(i)/[(\sqrt{\Sigma w_{lib}(i)*w_{lib}(i)})*(\sqrt{\Sigma w_{unk}(i)*w_{unk}(i)})]$$

where the denominator normalizes each spectrum to unit vector length. As a result, the dot product is restricted between a value of zero (0) and a value of one (1). In this instance, a dot product having a value of one (1) indicates the spectra are identical, while a dot product having a value of zero (0) indicates the spectra share no similarity. As seen, the numerator will increase when the ith mass fragment is present in both the unknown mass spectrum and the electronic database entry. In some instances, an allowance for ion chemistry can be incorporated into the algorithm (e.g., as previously described).

Then, a score can be determined using the comparison of the unknown mass spectrum to the electronic database entry (Block 360). For example, a final hit score can be determined using a metric determined as previously described, a combination of two or more metrics, and/or a weighted combination of two or more metrics. In a particular instance, a score can be calculated using the percent mass fragment match (fragMatch), the variance match (varMatch), and the weighted dot product (wDP) as follows:

$$score=a*fragMatch+b*varMatch+c*wDP$$

where the sum of the coefficients (a, b, c) is equal to a value of (1), which restricts the range of score values between values of zero (0) and one (1). In this particular instance, a higher score equates to a better match between the unknown sample and an electronic database entry, and the sample can be identified accordingly.

It shall be understood that the present invention is not limited to the exemplary embodiments disclosed herein, and that various changes, equivalents and combinations may be contemplated by those of ordinary skill in the pertinent art without departing from the scope of the claims. For example, the present invention is not limited to toroidal ion traps as described for exemplary embodiments, as the problem addressed is generic to all ion traps that produce non-classical spectra. As used herein, the term "approximately" shall mean approximately and/or exactly with respect to the value or range of values specified. Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A gas chromatography-mass spectroscopy (GC-MS) system for identifying an unknown sample, the GC-MS system comprising:
 a gas chromatograph configured to determine experimental chromatographic data for a calibration sample and an unknown sample, the experimental chromatographic data comprising a first retention time associated with the calibration sample and a second retention time associated with the unknown sample;
 a mass spectrometer configured to determine experimental mass spectral data for the unknown sample, the experimental mass spectral data comprising a mass spectrum associated with the unknown sample;

a processor communicatively coupled with the gas chromatograph and the mass spectrometer for receiving the experimental chromatographic data and the experimental mass spectral data; and a memory having computer executable instructions stored thereon, the computer executable instructions configured for execution by the processor to:

determine a retention index for the unknown sample based upon the first retention time associated with the calibration sample and the second retention time associated with the unknown sample, identify a subset of a plurality of database entries included in an electronic database comprising reference mass spectral data using the retention index determined for the unknown sample, compare the experimental mass spectral data to the subset of the plurality of database entries to identify the unknown sample; and initiate an alert when the identification of the unknown sample is associated with a sample of interest.

2. The GC-MS system as recited in claim 1, wherein the retention index comprises at least one of a plurality of retention times or a range of retention times.

3. The GC-MS system as recited in claim 1, wherein the mass spectrometer comprises a quadrupole field ion trap.

4. The GC-MS system as recited in claim 3, wherein the mass spectrometer comprises a toroidal ion trap.

5. The GC-MS system as recited in claim 1, wherein comparing the experimental mass spectral data to the subset of the plurality of database entries to identify the unknown sample comprises:

determining a percent fragment match between the experimental mass spectral data and the plurality of database entries.

6. The GC-MS system as recited in claim 1, wherein comparing the experimental mass spectral data to the subset of the plurality of database entries to identify the unknown sample comprises:

determining a variance match between the experimental mass spectral data and the plurality of database entries.

7. A computer-implemented method for identifying an unknown sample, the computer-implemented method comprising:

receiving experimental chromatographic data for a calibration sample and an unknown sample, the experimental chromatographic data comprising a first retention time associated with the calibration sample and a second retention time associated with the unknown sample;

determining a retention index for the unknown sample based upon the first retention time associated with the calibration sample and the second retention time associated with the unknown sample;

identifying a subset of a plurality of database entries included in an electronic database comprising reference mass spectral data using the retention index determined for the unknown sample;

receiving experimental mass spectral data for the unknown sample, the experimental mass spectral data comprising a mass spectrum associated with the unknown sample;

causing a processor to compare the experimental mass spectral data to the subset of the plurality of database entries to identify the unknown sample; and initiating an alert when the identification of the unknown sample is associated with a sample of interest.

8. The computer-implemented method as recited in claim 7, wherein the retention index comprises at least one of a plurality of retention times or a range of retention times.

9. The computer-implemented method as recited in claim 7, wherein the experimental mass spectral data for the unknown sample is collected using a quadrupole field ion trap.

10. The computer-implemented method as recited in claim 9, wherein the experimental mass spectral data for the unknown sample is collected using a toroidal ion trap.

11. The computer-implemented method as recited in claim 7, wherein comparing the experimental mass spectral data to the subset of the plurality of database entries to identify the unknown sample comprises:

determining a percent fragment match between the experimental mass spectral data and the plurality of database entries.

12. The computer-implemented method as recited in claim 7, wherein comparing the experimental mass spectral data to the subset of the plurality of database entries to identify the unknown sample comprises:

determining a variance match between the experimental mass spectral data and the plurality of database entries.

13. A computer-readable storage medium having computer executable instructions for identifying an unknown sample, the computer executable instructions comprising:

receiving experimental chromatographic data for a calibration sample and an unknown sample, the experimental chromatographic data comprising a first retention time associated with the calibration sample and a second retention time associated with the unknown sample;

determining a retention index for the unknown sample based upon the first retention time associated with the calibration sample and the second retention time associated with the unknown sample;

identifying a subset of a plurality of database entries included in an electronic database comprising reference mass spectral data using the retention index determined for the unknown sample;

receiving experimental mass spectral data for the unknown sample, the experimental mass spectral data comprising a mass spectrum associated with the unknown sample; and comparing the experimental mass spectral data to the subset of the plurality of database entries to identify the unknown sample using at least one of a percent fragment match or a variance match between the experimental mass spectral data and the plurality of database entries.

14. The computer-readable storage medium as recited in claim 13, wherein the retention index comprises at least one of a plurality of retention times or a range of retention times.

15. The computer-readable storage medium as recited in claim 13, wherein the experimental mass spectral data is received from a quadrupole field ion trap.

16. The computer-readable storage medium as recited in claim 15, wherein the experimental mass spectral data is received from a toroidal ion trap.

17. The computer-readable storage medium as recited in claim 13, wherein comparing the experimental mass spectral data to the subset of the plurality of database entries to identify the unknown sample comprises using the percent fragment match and the variance match between the experimental mass spectral data and the plurality of database entries.

18. The computer-readable storage medium as recited in claim 17, wherein the computer executable instructions further comprise identifying the unknown sample using a weighted combination of the percent fragment match and the variance match.

19. The computer-readable storage medium as recited in claim 13, wherein the computer executable instructions comprise initiating an alert when the identification of the unknown sample is associated with a sample of interest.

* * * * *